United States Patent
Nishimura

(10) Patent No.: US 10,108,002 B2
(45) Date of Patent: Oct. 23, 2018

(54) OPTICAL SCANNING IMAGE FORMING APPARATUS AND OPTICAL SCANNING IMAGE FORMING METHOD

(71) Applicant: OLYMPUS CORPORATION, Tokyo (JP)

(72) Inventor: Junichi Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 216 days.

(21) Appl. No.: 15/191,776

(22) Filed: Jun. 24, 2016

(65) Prior Publication Data

US 2016/0306164 A1    Oct. 20, 2016

Related U.S. Application Data

(63) Continuation of application No. PCT/JP2014/006462, filed on Dec. 25, 2014.

(30) Foreign Application Priority Data

Dec. 26, 2013    (JP) .................................. 2013-270108

(51) Int. Cl.
*A61B 1/04* (2006.01)
*A61B 1/06* (2006.01)
(Continued)

(52) U.S. Cl.
CPC ...... *G02B 23/2469* (2013.01); *A61B 1/00009* (2013.01); *A61B 1/00172* (2013.01);
(Continued)

(58) Field of Classification Search
CPC .............. G02B 23/2469; G02B 26/103; G02B 23/2484; G02B 26/10; G02B 23/26;
(Continued)

(56) References Cited

U.S. PATENT DOCUMENTS

| 2009/0028407 A1* | 1/2009 | Seibel | A61B 1/0008 |
| | | | 382/131 |
| 2010/0137684 A1* | 6/2010 | Shibasaki | A61B 1/00009 |
| | | | 600/109 |
| 2010/0157036 A1* | 6/2010 | Sugimoto | A61B 1/00009 |
| | | | 348/65 |

FOREIGN PATENT DOCUMENTS

| JP | 4672023 B2 | 4/2011 |
| JP | 2012-152244 A | 8/2012 |

(Continued)

OTHER PUBLICATIONS

Chinese Office Action dated May 4, 2017 in Chinese Patent Application No. 201480070948.2.
(Continued)

*Primary Examiner* — Jared Walker
(74) *Attorney, Agent, or Firm* — Scully, Scott, Murphy & Presser, P.C.

(57) ABSTRACT

Provided is an optical scanning image forming apparatus, including: a light source section; an illumination scanning section scanning illumination light from the light source section and irradiating the illumination light onto an object; a light detection section detecting detection light from the object; a calculation section calculating a drive waveform for providing a light scanning pattern to be formed by the illumination scanning section; and a coordinate for image construction; and an image drawing section drawing an image based on the detection light detected by the light detection section and the coordinate for image construction, the drive waveform consisting of, in a predetermined period, a plurality of frames of different phases. Also provided is an optical scanning image forming method.

9 Claims, 9 Drawing Sheets

(51) Int. Cl.
| | |
|---|---|
| *G02B 23/24* | (2006.01) |
| *G02B 23/26* | (2006.01) |
| *G02B 26/10* | (2006.01) |
| *A61B 1/00* | (2006.01) |
| *A61B 1/045* | (2006.01) |
| *H04N 5/225* | (2006.01) |

(52) U.S. Cl.
CPC .......... *A61B 1/045* (2013.01); *G02B 23/2484* (2013.01); *G02B 23/26* (2013.01); *G02B 26/10* (2013.01); *G02B 26/103* (2013.01); *H04N 5/2256* (2013.01)

(58) Field of Classification Search
CPC .. H04N 5/2256; A61B 1/045; A61B 1/00172; A61B 1/00009
USPC .......................................................... 348/68
See application file for complete search history.

(56) References Cited

FOREIGN PATENT DOCUMENTS

| | | | |
|---|---|---|---|
| JP | 2012-231911 A | | 11/2012 |
| JP | 2012231911 | * | 11/2012 |

OTHER PUBLICATIONS

Extended Supplementary European Search Report dated Oct. 30, 2017 in European Patent Application No. 14 87 3796.8.
International Search Report dated Mar. 24, 2015 issued in PCT/JP2014/006462.
Japanese Office Action dated Aug. 15, 2017 in Japanese Patent Application No. 2013-270108.

* cited by examiner

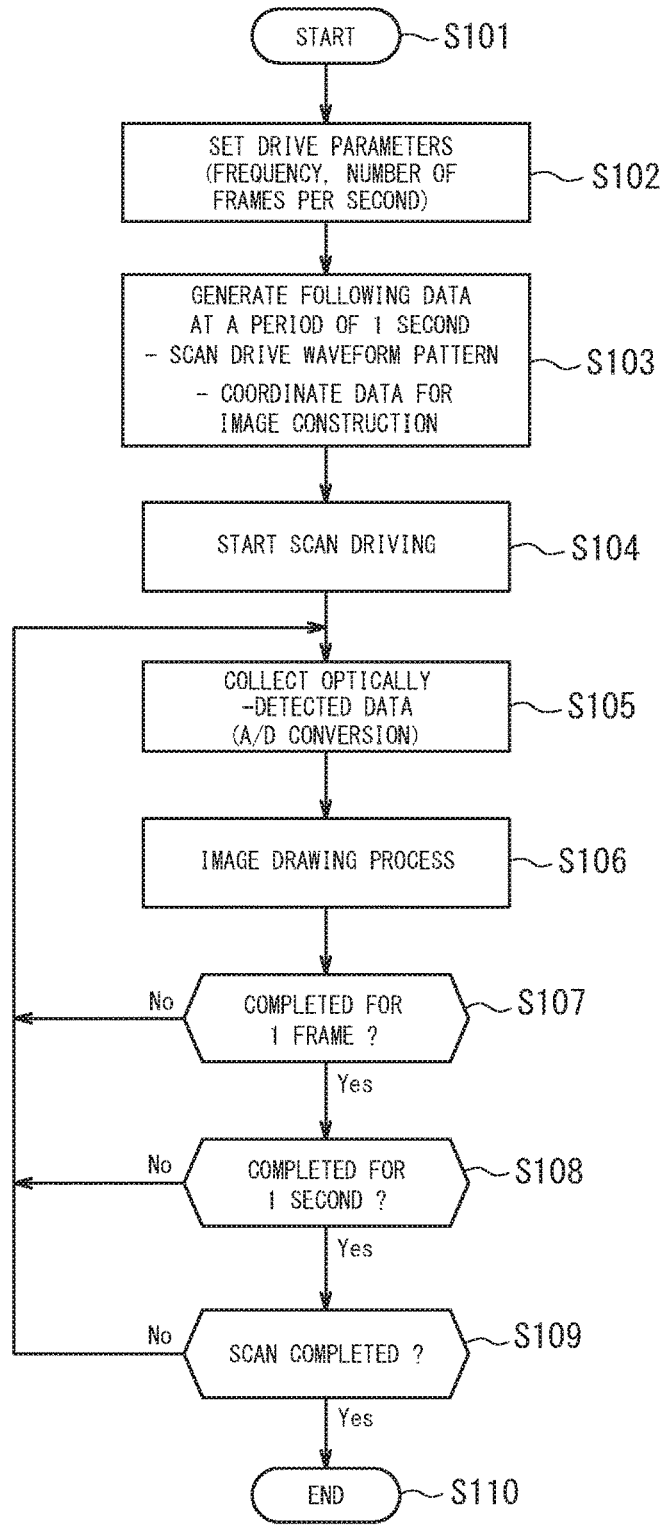

OPTICAL SCANNING IMAGE FORMING APPARATUS AND OPTICAL SCANNING IMAGE FORMING METHOD

CROSS-REFERENCE TO RELATED APPLICATION

The present application is a Continuing Application based on International Application PCT/JP2014/006462 filed on Dec. 25, 2014, the entire disclosure of which is incorporated herein by reference.

TECHNICAL FIELD

The present disclosure relates to an optical scanning image forming apparatus and an optical scanning image forming method.

BACKGROUND ART

There has been hitherto known an optical scanning-type image forming apparatus which scans illumination light from the tip part of an optical fiber toward an object and detects detection light reflected and scattered by the object or fluorescence generated in the object (see, for example, Patent Literature 1). In such apparatus, the optical fiber is held in part with the tip part for emitting the illumination light being oscillatable, and an actuator is disposed in the vicinity of the supporting part, so as to vibrate the optical fiber, to thereby scan the illumination light on the object.

CITATION LIST

Patent Literature

PTL 1: JP4672023B

SUMMARY

The disclosed optical scanning image forming apparatus includes: a light source section; an illumination scanning section scanning illumination light from the light source section and irradiating the illumination light onto an object; a light detection section detecting detection light from the object; a calculation section calculating: a drive waveform for providing a light scanning pattern to be formed by the illumination scanning section; and a coordinate for image construction; and an image drawing section drawing an image based on the detection light detected by the light detection section and the coordinate for image construction, the drive waveform consisting of, in a predetermined period, a plurality of frames of different phases.

In the disclosed optical scanning image forming apparatus, the predetermined period may preferably be 1 second.

Further, in the disclosed optical scanning image forming apparatus, the drive waveform may preferably be smoothly connected across the frames.

Here, "smoothly connected" means that the drive waveform is continuous across the frames.

Still further, in the disclosed optical scanning image forming apparatus, the drive waveform may preferably have a constant frequency in the period.

Here, the "constant frequency" also refers to a fundamental frequency that remains constant when modulated.

Here, in the disclosed optical scanning image forming apparatus, the image drawing section may preferably form an image for each frame according to a drive waveform specific to the frame.

Further, in the disclosed optical scanning image forming apparatus, the drive waveform may preferably be different only in phase across the frames.

Here, in the disclosed optical scanning image forming apparatus, the drive waveform may preferably vary with time either in amplitude, frequency, or phase.

Further, in the disclosed optical scanning image forming apparatus, in a case where the drive waveform varies with time in amplitude, the drive waveform may preferably have an envelope in the same shape across the frames.

Still further, in the disclosed optical scanning image forming apparatus, in a case where the drive waveform varies with time in frequency, the drive waveform may preferably have an envelope repeated at intervals of the period.

Further, the disclosed optical scanning image forming apparatus may preferably be applied to an optical scanning endoscope.

Here, the disclosed optical scanning image forming method includes the steps of: setting a drive frequency, a period, and the number of frames in 1 period of a drive waveform for providing a light scanning pattern; generating, based on the set drive frequency and period, the drive waveform and coordinate data for image construction; scanning an illumination light according to the light scanning pattern provided by the generated drive waveform; detecting detection light from an object; and drawing an image based on the detected detection light and the coordinate data for image construction.

BRIEF DESCRIPTION OF DRAWINGS

In the accompanying drawings:

FIG. 9 is a flowchart of an embodiment of the disclosed optical scanning image forming method.

DESCRIPTION OF EMBODIMENTS

The following describes embodiments of the disclosed apparatus and method, with reference to the drawings.

Figure 1:
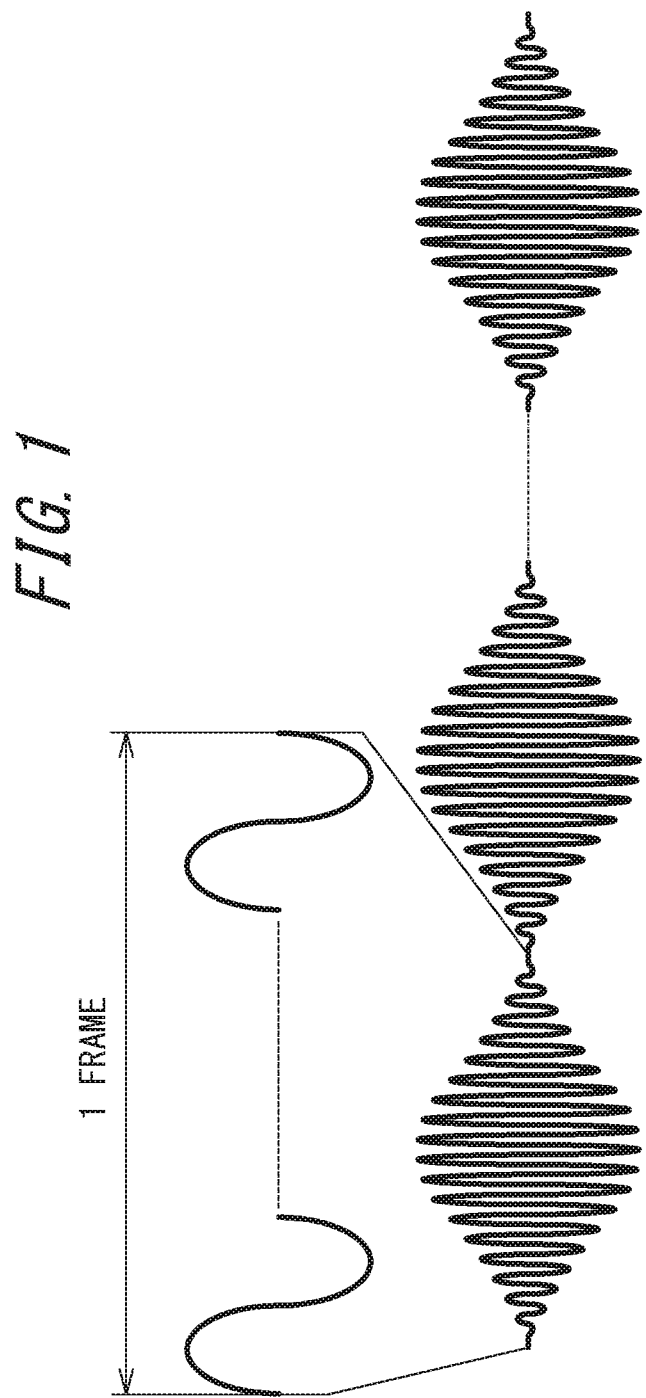
FIG. 1 shows a conventional drive waveform.
Figure 2:
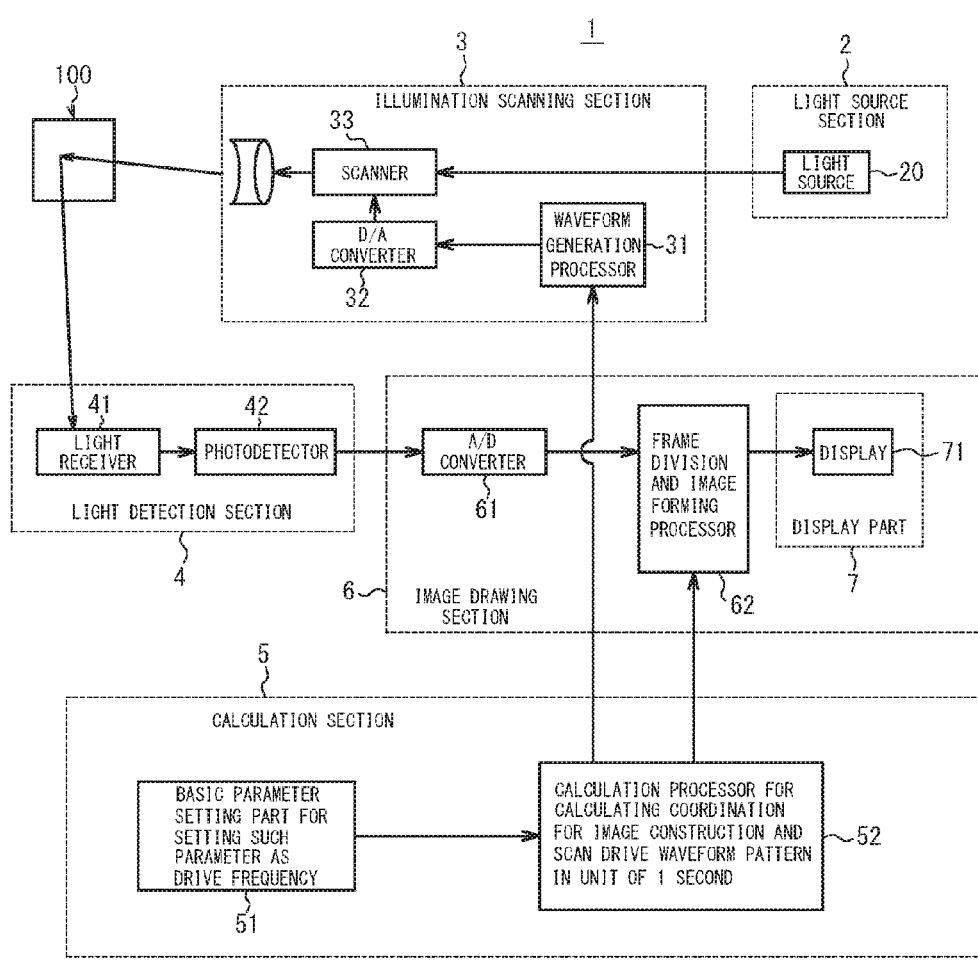
FIG. 2 is a block diagram of an embodiment of the disclosed optical scanning image forming apparatus.

FIG. 2 is a block diagram of an embodiment of the disclosed optical scanning image forming apparatus (endoscope apparatus). As illustrated in FIG. 2, the optical scanning image forming apparatus 1 includes: a light source section 2; an illumination scanning section 3 scanning illumination light from the light source 2 and irradiating the light onto an object; a light detection section 4 detecting detection light from the object; a calculation section 5 for calculating a drive waveform for providing a light scanning pattern to the illumination scanning section 3 and a coordinate for image construction; an image drawing section 6 drawing an image based on the detection light detected by the light detection section 4 and the coordinate for image construction; and a display part 7.

The light source section 2 has a light source 20, and multiplexes lights from, for example, three laser light sources emitting continuous wave (CW) laser lights of three primary colors of red, green, and blue, so as to emit the multiplexed light as white light. Examples for use as the laser light sources may include, for example, a diode pumped solid state (DPSS) laser and a laser diode. Needless to say, the light source 20 may employ one laser light source or a plurality of other light sources, without being limited to the aforementioned configuration.

Figure 3:
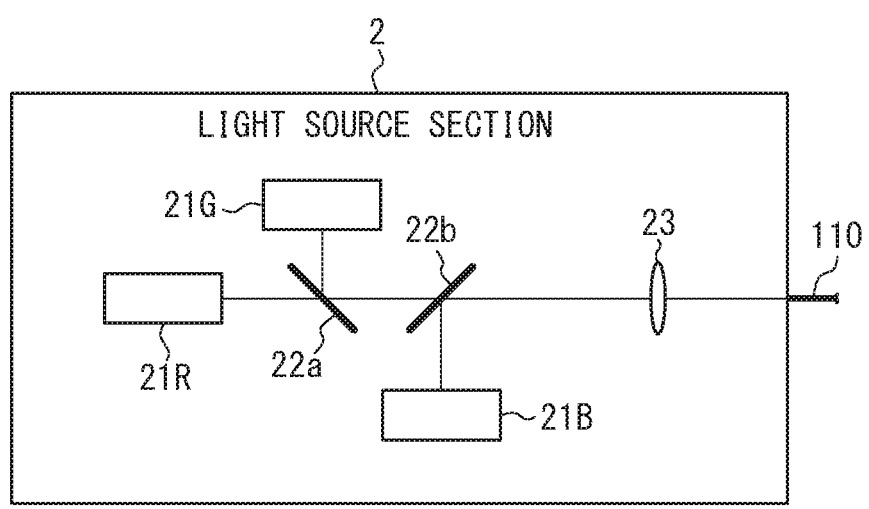
FIG. 3 is a diagram illustrating a schematic configuration of the light source section.

FIG. 3 is a diagram illustrating a schematic configuration of the light source section 2. The light source section 2 includes laser light sources 21R, 21G, 21B emitting continuous wave (CW) of three primary colors of red, green, and blue; dichroic mirrors 22a, 22b; and a lens 23. The red laser light source 21R may employ, for example, a semiconductor laser (laser diode (LD)). The green laser light source 21G may employ a diode pumped solid state (DPSS) laser. The blue laser light source 21B may employ, for example, a laser diode (LD).

A red laser light emitted from the laser light source 21R emits a red laser light, which sequentially passes through the dichroic mirror 22a and the dichroic mirror 22b. The laser light source 21G emits green laser light, which is reflected by the dichroic mirror 22a and coaxially multiplexed with the red laser light so as to pass through the dichroic mirror 22b. The laser light source 21B emits blue laser light, which is reflected by the dichroic mirror 22b, and coaxially multiplexed with red laser light and green laser light. In this manner, the dichroic mirror 22b emits white laser light obtained by multiplexing laser lights of three primary colors of red, green, blue.

The laser light sources 21R, 21G, 21B and the dichroic mirrors 22a, 22b are not be limitedly configured as in FIG. 3, and may be configured, for example, to first multiplex green and blue laser lights, which may then be multiplexed with red laser light.

Returning to FIG. 2, the illumination scanning section 3 includes: a waveform generation processor 31 generating a drive waveform, based on the calculation results obtained in the calculation section 5; a D/A converter 32 D/A converting the drive waveform; and a scanner 33 scanning illumination light from the light source section 2 to irradiate an object with the light.

Figure 4:
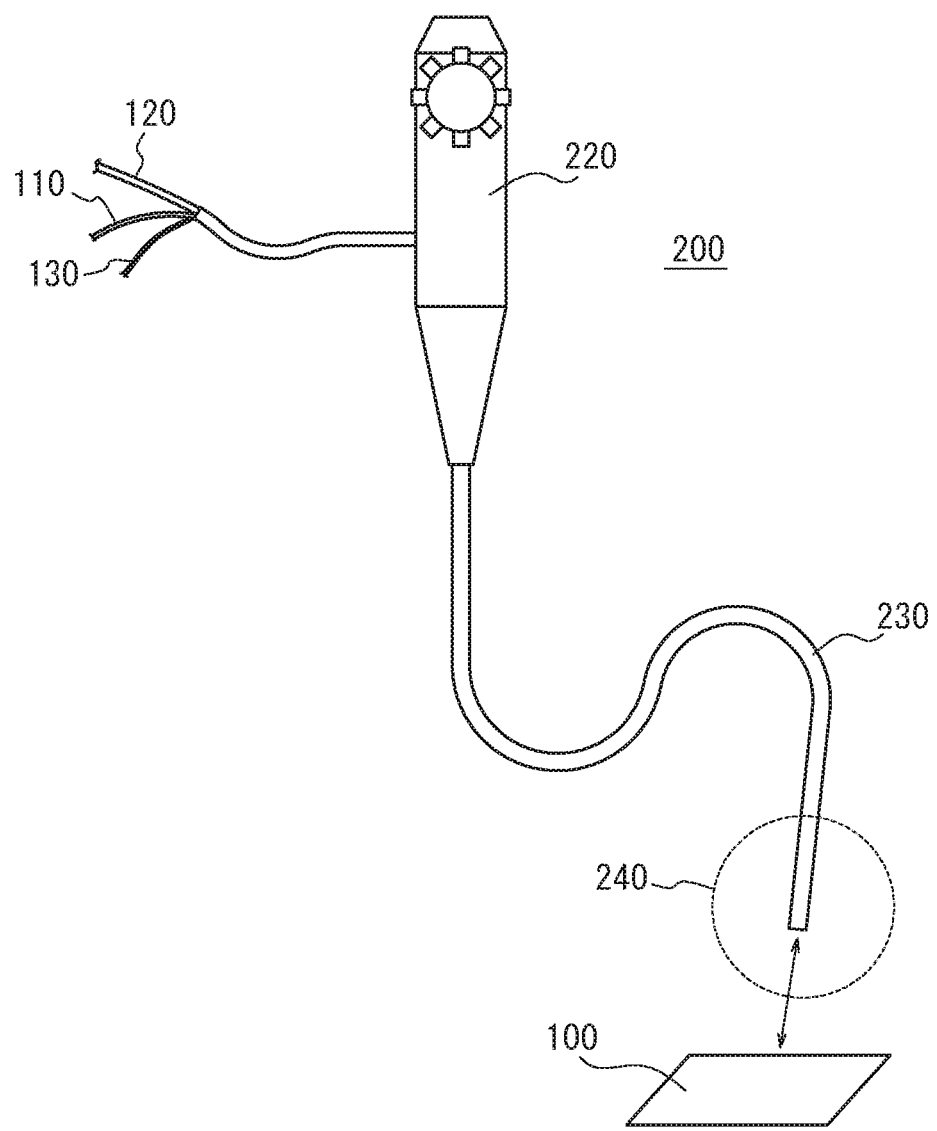
FIG. 4 is a schematic overview of the scope of the optical scanning image forming apparatus.

Here, FIG. 4 is a schematic overview of a scope of an endoscope apparatus. The scanner 33 is disposed at the tip part 240 (enclosed by the dashed line of FIG. 4) of the scope 200. As illustrated in FIG. 4, as an example, the scope 200 includes an operation portion 220 and an insertion portion 230, in which the operation portion 220 is connected at one end thereof to the one end of the insertion portion 230 so as to be integrally formed therewith. The operation portion 220 has an illumination optical fiber 110 from the light source section 2, a detection optical fiber bundle 120 from the detection section 4, and a wiring cable 130 from the D/A converter 32 to the scanner 33 each connected thereto. The illumination optical fiber 110, the detection optical fiber bundle 120, and the wiring cable 130 are guided, through the inside of the insertion portion 230, to a tip part 240, another tip part different from the tip part connected to the operation portion 220 of the insertion portion 230.

Figure 5:
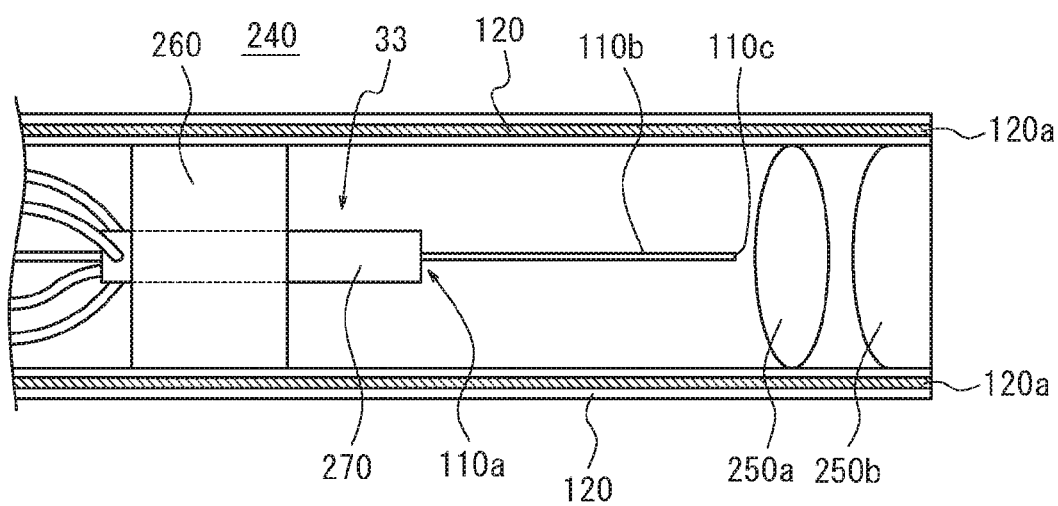
FIG. 5 is a sectional view of the tip part of the scope of the optical scanning image forming apparatus of FIG. 4.

FIG. 5 is an enlarged sectional view of the tip part 240 of the insertion portion 230 of the scope 200 of FIG. 4. The tip part 240 includes: a scanner 33, projection lenses 250a, 250b, and a detection lens (not shown), while having an illumination optical fiber 110 and a detection optical fiber bundle 120 extending through the insertion portion 230.

Figure 6A:
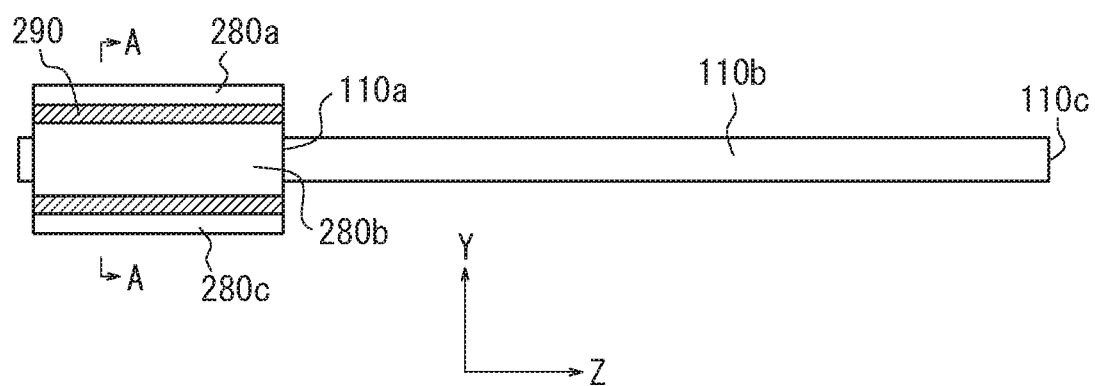
FIG. 6A is a side view of the vibratory drive mechanism of an optical scanning endoscope apparatus and the oscillation part of the illumination optical fiber.
Figure 6B:
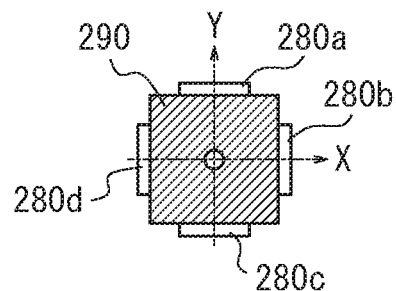
FIG. 6B is a sectional view taken along the line A-A of FIG. 6A.

The scanner 33 is configured by including: an actuator tube 270 fixed inside the insertion portion 230 of the scope 200 via an attachment ring 260; and piezoelectric elements 280a to 280d and a fiber holding member 290 arranged inside the actuator tube 270 (see FIGS. 6A and 6B). The illumination optical fiber 11, which is supported by the fiber holding member 290, has an oscillation part 11b oscillatably supported, the oscillation part 11b being defined between the fixed end 110a supported by the fiber holding member 290 and the tip part 110c. Meanwhile, the detection optical fiber bundle 120 is disposed so as to pass through the circumferential part of the insertion portion 230 to extend to the tip end of the tip part 240.

Further, the projection lenses 250a, 250b and the detection lens are disposed at an extreme tip of the tip part 240. The projection lenses 250a, 250b are configured such that laser light emitted from the tip part 110c of the illumination optical fiber 110 is substantially converged on an observation object 100. Further, the detection lens is disposed to take in the laser light that has been reflected, scattered, and refracted by the object 100 (light that has been interacted with the observation object 100) after being converged on the observation object 100, so as to converge and couple the laser light to the detection optical fiber bundle 120 disposed behind the detection lens. Here, one projection lens or a plurality of other lenses may constitute the projection lens system, without being limited to the two-lens configuration.

FIG. 6A illustrates a vibratory drive mechanism of the optical scanning image forming apparatus 1 and the oscillation part 110b of the illumination optical fiber 110, FIG. 6B is a sectional view taken along the line A-A of FIG. 6A, and FIG. 6C is a sectional view taken along the line B-B of FIG. 6A. The illumination optical fiber 110 penetrates the center of the fiber holding member 290 in a prism shape, so as to be fixed and held by the fiber holding member 290. Accordingly, the illumination optical fiber 110 has a fixed part thereof penetrating the fiber holding member 290. The fiber holding member 290 has four side faces each facing the +Y direction and the +X direction and the directions opposite thereto, respectively. Then, the fiber holding member 290 has, in the +Y and −Y directions, a pair of the Y-direction driving piezoelectric elements 280a, 280c fixed thereon, while having, in the +X and −X directions, a pair of the X—direction driving piezoelectric elements 280b, 280d fixed thereon.

The piezoelectric elements 280a to 280d are each connected with the wiring cable 130. A drive voltage generator applies voltages to the X-direction driving piezoelectric elements 280b, 280d and to the Y-direction driving piezoelectric elements 280a, 280c at independently different driving frequencies, to thereby vibratory drive the piezoelectric elements. When the Y-direction driving piezoelectric elements 280a, 280c and the X-direction driving piezoelectric elements 280b, 280d are each vibratory driven, the oscillation part 110b of the illumination optical fiber 110 is vibrated and the tip part 110c is deflected, and thus, laser light emitted from the tip part 110 sequentially scans the surface of the observation object 100.

Returning to FIG. 2, the light detection section 4 has a light receiver 41 receiving detection light reflected/scattered by the object or detection light such as fluorescence generated by the object, and a photodetector 42 detecting the received detection light. For example, the photodetector 42 decomposes signal light transmitted through the optical fiber bundle 120 into its spectral components, and photoelectrically converts the decomposed signal light.

Figure 7:
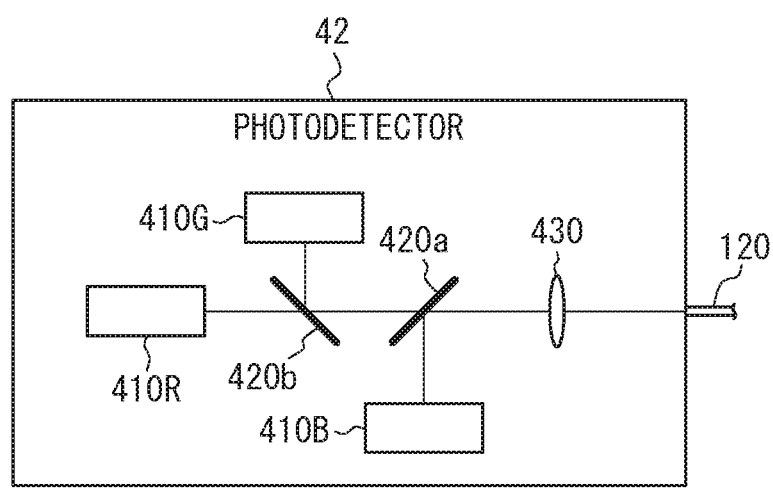
FIG. 7 illustrates a schematic configuration of the light detection section.

FIG. 7 illustrates a schematic configuration of the photodetector 42. The photodetector 42 includes: light receivers 410R, 410G, 410B for detecting light corresponding to each color of red, green, or blue; dichroic mirrors 420a, 420b; and a lens 430. The optical fiber bundle 120 is connected to the photodetector 42.

The lens 430 converts signal light emitted from an emitting end of the optical fiber bundle 120 into substantially parallel light fluxes, of which light in the wavelength range of blue is reflected and separated by the dichroic mirror 420a while lights in the wavelength ranges of red and green pass through the dichroic mirror 420a. The light in the wavelength range of blue separated by the dichroic mirror 420a is received by the light receiver 410B and photoelectrically converted. The lights in the wavelength ranges of red and green that have passed through the dichroic mirror 420a are separated by the dichroic mirror 420b which reflects light in the wavelength range of green while transmitting light in the wavelength range of red. The green and red signal lights separated by the dichroic mirror 420b are each received by the light receiver 410G and the light receiver 410R, respectively, and photoelectrically converted.

The photoelectrically-converted outputs from the light receivers 410R, 410G, and 410B are input to the image drawing section 6. Here, the light receivers 410R, 410G, 410B and the dichroic mirrors 420a, 420b may be arranged, without being limited to the configuration of FIG. 7, so as to separate, for example, a red light from the signal light, and then further to separate green and blue lights.

Returning again to FIG. 2, the calculation section 5 includes: a basic parameter setting part 51 capable of setting basic parameters to be given to actuators such as the piezoelectric elements 280a to 280d such as drive frequency, period, and the number of frames per 1 period of the drive waveform; and a calculation processor 52 calculating, based on the set parameters, a drive waveform and a coordinate for image construction. Then, the calculated drive waveform is sent to the waveform generation processor 31 of the illumination scanning section 3, and given a light scanning pattern to be formed by the illumination scanning section 3. Here, in this embodiment, the drive waveform calculated by the calculation section 5 has a feature in that the period is 1 second, and the period has a plurality of frames of different phases. The calculated coordinate for image construction is sent to the image drawing section 6.

When the optical scanning image forming apparatus 1 is operated for observation, the waveform generation processor 31 is driven under the control of the calculation section 5, so as to apply vibration voltage via the wiring cable 130 to the piezoelectric elements 280a to 280d constituting the scanner 33, to thereby vibrates the oscillation part 110b of the illumination optical fiber 110. In the case of raster scan, for example, the Y-direction driving piezoelectric elements 280a, 280c are vibratory driven, for example, at several kHz which is the resonance frequency in the Y direction of the oscillation part 110b of the illumination optical fiber 110, while the X-direction driving piezoelectric elements 280b, 280d are vibratory driven at a non-resonance frequency of, for example, about 30 Hz, which is considerably slower than the resonance frequency in the Y direction.

Next, as illustrated in FIG. 2, the image drawing section 6 converts light detected by the light detection section 4 into a digital signal through an A/D converter 61. Then, the digital signal and the coordinate for image construction calculated by the calculation section 5 are received by a functional part 62, which divides the frames based on the information thus received, allocates the obtained image data to each frame, and displays the image on the display 71 of the display part 7.

Herein, the drive waveform calculated by the calculation section 5 needs to have a plurality of frames of different phases in a predetermined period.

Figure 8:
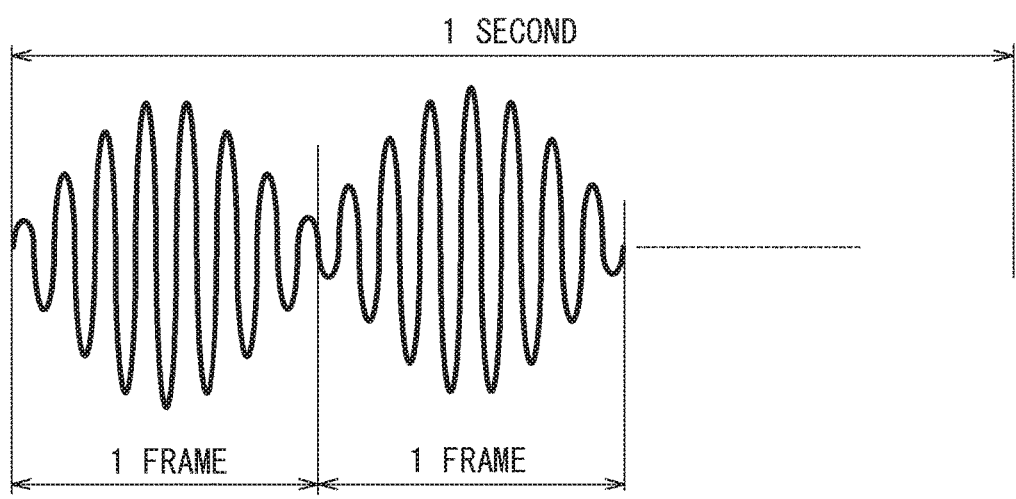
FIG. 8 shows an embodiment of the disclosed drive waveform.

In the example of FIG. 8, the drive waveform has a period of 1 second and a plurality of frames in 1 second, and is different in phase across the adjacent frames. In other words, for example, the waveform is different in phase at the starting points in the frames, while coherent in phase at the starting point and the end point (not shown) in 1 second as a period.

As described above, the drive waveform is constructed in the unit of periods, rather than in the unit of frames, so as to impart a degree of freedom to the drive waveform for each frame, which allows detailed setting of the drive frequency in small unit of, for example, 1 Hz, irrespective of the number of frames. Therefore, the actuator can be driven and a coordinate can be constructed at an optimum frequency. In particular, in the case of two-dimensional scan with a Lissajous' waveform, the frequency difference between the two axes constitutes elements for the coordinate for image construction and the scan locus. Thus, the drive frequency can preferably be set for each 1 Hz.

Further, in order to make smooth the movement of the scanning pattern, the drive waveform may preferably be smoothly connected across the frames, or may preferably have a constant frequency in a period, and in particular, may preferably be different only in phase across the frames.

Further, as illustrated in FIG. 8, when the drive waveform varies with time in frequency, the drive waveform may preferably have an envelope in the same shape across the frames, and the envelope of the drive waveform may preferably be repeated for each period, because it can make smooth the movement of the scanning pattern in varying the amplitude. Here, in the example of FIG. 8, the drive waveform varies with time in frequency. However, in the disclosed apparatus or method, the drive waveform may vary with time either in amplitude, frequency, or phase.

Here, the image drawing section 6 may preferably form an image for each frame according to the drive waveform specific to the frame.

This configuration allows for forming an image for each frame in accordance with the drive waveform thereof, even if the drive waveform varies for each frame as disclosed herein.

Next, an embodiment of the disclosed optical scanning image forming method is described with reference to FIGS. 2 and 9.

When the method is started (Step S101), the basic parameter setting part 51 of the calculation section 5 first sets drive parameters (Step S102). The drive parameters include the drive frequency of the actuators and the number of frames per 1 second. Here, the period, which is defined as 1 second in this embodiment, may also be defined otherwise. In such case, the number of frames is defined per period.

Next, the calculation processor 52 generates data on the drive waveform and the coordinate for image construction per a period of 1 second (Step S103). Of the data, the data on the drive waveform is sent to the waveform generation processor 31 of the illumination scanning section 3, and given a light scanning pattern to be formed by the illumination scanning section 3. Meanwhile, the data on the coordinate for image construction is sent to the image forming processor 62 of the image drawing section 6.

Next, in the illumination scanning section 3, the digital signals of the aforementioned scanning pattern is D/A converted by the D/A converter 32, and the scanner 33 starts scan-driving (Step S104).

When the object 100 is irradiated with illumination light scanned by the scanner 33, the object 100 may reflect/scatter the illumination light or generate fluorescence. Then, the light receiver 41 of the light detection section 4 receives the reflected light, the scattered light, and the fluorescence, which are photoelectrically converted by the photodetector 42 as described above.

The photoelectrically-converted analog electric signal is sent from the light detection section 4 to the image drawing section 6 where the signal is converted into a digital signal by the A/D converter 61 (Step S105). Then, the functional part 62 that has received the coordinate for image construction divides the frames based on the information, allocates the obtained image data (the aforementioned digital signal) to each frame, and displays the image on the display 71 of the display part 7 (Step S106).

Steps S105, S106 are repeated until the processing for one frame is completed (Step S107). Then, when the processing for one frame is completed, Steps S105 to S107 are repeated until the processing for 1 second is completed (Step S108).

When the processing for 1 second is completed, it is determined whether the scanning has been completed (Step S109). When the scanning has not been completed, Steps S105 to S107 are repeated, and when the scan has been completed, the series of the flow is ended (Step S110).

The optical scanning image forming method according to the aforementioned embodiment allows for detailed setting of the drive frequency, in particular, for detailed setting of the drive frequency near the resonance frequency.

Embodiments of the disclosed apparatus and method have been described as above, which however should not be construed as limiting the present disclosure. For example, the scanning pattern is not limited to a raster waveform, and various scanning patterns including a Lissajous waveform and a spiral waveform may be applicable. The scanner is not limited to the one using piezoelectric elements, and various scanners such as a scanner driven by electromagnetic force may be applied. Further, the scanner is not limited to an optical fiber type scanner which is driven by vibrating an optical fiber.

REFERENCE SIGNS LIST 1 optical scanning image forming apparatus
2 light source section
3 illumination scanning section
4 light detection section
5 calculation section
6 image drawing section
7 display part

The invention claimed is:

1. An optical scanning image forming apparatus, comprising:
  a light source configured to emit illumination light;
  an actuator configured to scan the illumination light emitted by the light source and irradiate the illumination light onto an object;
  a photodetector configured to detect detection light from the object; and
  a processor configured to:
    calculate a drive waveform for providing a light scanning pattern to be formed by the actuator;
    calculate a coordinate for image construction; and
    form an image based on the detection light detected by the light detector and the coordinate for image construction,
  wherein the drive waveform has a constant frequency,
  wherein the drive waveform comprises a plurality of portions in a predetermined period, wherein the plurality of portions of the drive waveform correspond to a plurality of frames of images to be formed,
  wherein a phase of each of the plurality of portions of the drive waveform is different from one another, and
  wherein an end value of a portion of the drive waveform is continuous with a start value of a subsequent adjacent portion of the drive waveform.

2. The optical scanning image forming apparatus according to claim 1,
  wherein the predetermined period is 1 second.

3. The optical scanning image forming apparatus according to claim 1,
  wherein the processor is configured to form an image for each frame according to a drive waveform specific to the frame.

4. The optical scanning image forming apparatus according to claim 1,
  wherein the drive waveform is different only in phase across the frames.

5. The optical scanning image forming apparatus according to claim 1,
  wherein the drive waveform varies with time either in amplitude, frequency, or phase.

6. The optical scanning image forming apparatus according to claim 5,
  wherein, in a case where the drive waveform varies with time in amplitude, the drive waveform has an envelope in the same shape across the frames.

7. The optical scanning image forming apparatus according to claim 5,
  wherein, in a case where the drive waveform varies with time in frequency, the drive waveform has an envelope repeated at intervals of the predetermined period.

8. An optical scanning endoscope comprising:
  the optical scanning image forming apparatus according to claim 1.

9. An optical scanning image forming method, comprising the steps of:
  setting a drive frequency, a period, and the number of frames in 1 period of a drive waveform for providing a light scanning pattern;
  generating, based on the set drive frequency and period, the drive waveform and coordinate data for image construction;
  scanning an illumination light according to the light scanning pattern provided by the generated drive waveform;
  detecting detection light from an object; and
  forming an image based on the detected detection light and the coordinate data for image construction,
  wherein the drive waveform has a constant frequency,
  wherein the drive waveform comprises a plurality of portions in a predetermined period, wherein the plurality of portions of the drive waveform correspond to a plurality of frames of images to be formed, wherein a phase of each of the plurality of portions of the drive waveform is different from one another, and wherein an end value of a portion of the drive waveform is continuous with a start value of a subsequent adjacent portion of the drive waveform.

\* \* \* \* \*